United States Patent [19]

Bordoni et al.

[11] Patent Number: 4,510,929
[45] Date of Patent: Apr. 16, 1985

[54] DISPOSABLE RADIOACTIVE AEROSOL INHALATION APPARATUS

[76] Inventors: Maurice E. Bordoni, R.D. #1 (Horton Rd.), Westtown, N.Y. 10998; Ephraim Lieberman, 1 Victory Rd., Suffern, N.Y. 10901

[21] Appl. No.: 642,718

[22] Filed: Aug. 22, 1984

Related U.S. Application Data

[63] Continuation of Ser. No. 360,370, Apr. 30, 1982, abandoned.

[51] Int. Cl.³ .............................................. A61M 11/00
[52] U.S. Cl. .......................... 128/200.14; 128/200.21; 128/654
[58] Field of Search ...................... 128/200.14, 200.18, 128/200.19, 200.21, 654, 910, 1.1

[56] References Cited

U.S. PATENT DOCUMENTS

| | | | |
|---|---|---|---|
| 3,097,645 | 7/1963 | Lester | 128/200.21 |
| 3,172,406 | 3/1965 | Bird et al. | 128/200.21 |
| 3,666,955 | 5/1972 | Suprenant et al. | 128/654 |
| 3,695,254 | 10/1972 | Blum | 128/654 |
| 3,762,409 | 10/1973 | Lester | 128/200.14 |
| 3,769,967 | 11/1973 | Jones et al. | 128/654 |
| 3,777,742 | 12/1973 | Aumiller et al. | 128/654 |
| 3,881,463 | 5/1975 | Le Mon | 128/654 |
| 3,976,050 | 8/1976 | Glasser et al. | 128/654 |
| 4,116,387 | 9/1978 | Kremer, Jr. et al. | 128/200.18 X |
| 4,202,345 | 5/1980 | Farella et al. | 128/654 |
| 4,333,450 | 6/1982 | Lester | 128/200.14 |

Primary Examiner—Edward M. Coven
Attorney, Agent, or Firm—Leonard Bloom

[57] ABSTRACT

A disposable aerosol inhalation device for use in producing properly sized radioactive tagged particles. A mouthpiece is attached to a wye connector containing a valving system for inhalation of the radioactive aerosol and exhalation to an entrapping filter. Conduits are respectively provided by flexible tubing to a nebulizer and to the filter. The optimum range of particle sizes is generated by producing an aerosol from the nebulizer having an internal baffle. For ease of handling and to minimize radiation exposures, an entry is provided to add radioactive solution directly into the baffled nebulizer. To further reduce radiation exposure, the baffled nebulizer and entrapping filter are housed in a leaded enclosure.

8 Claims, 4 Drawing Figures

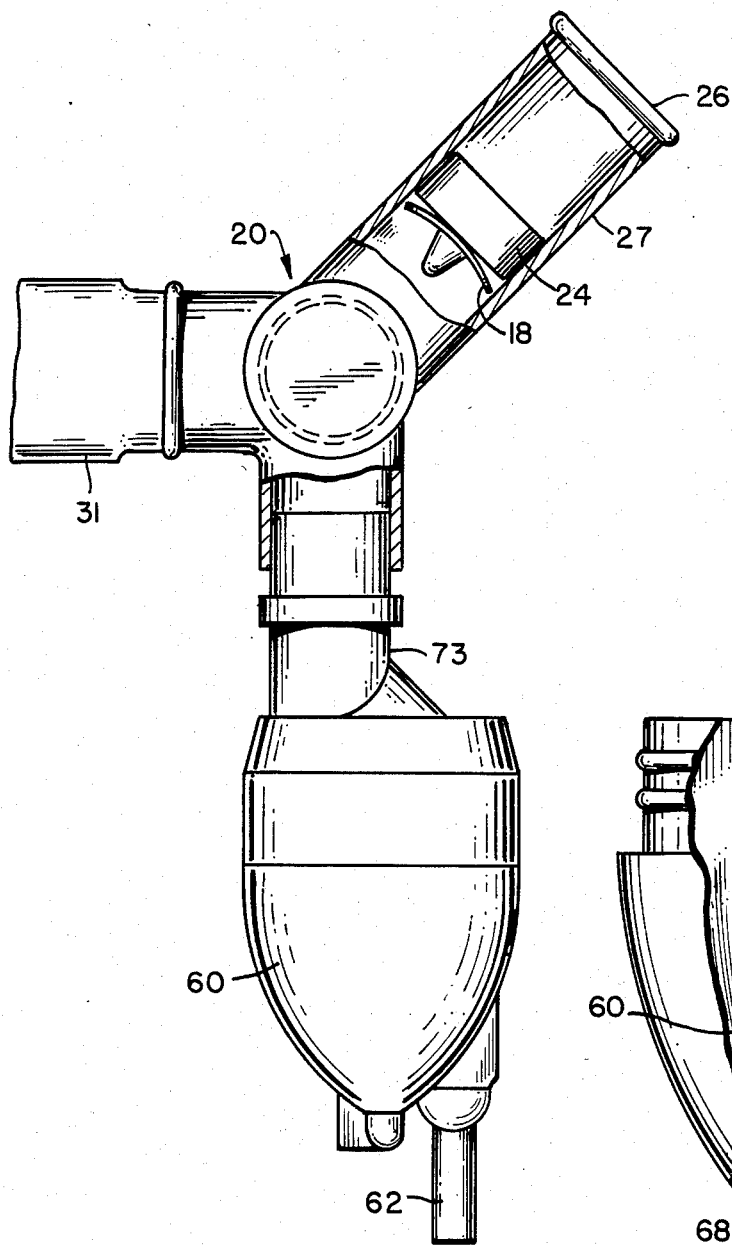
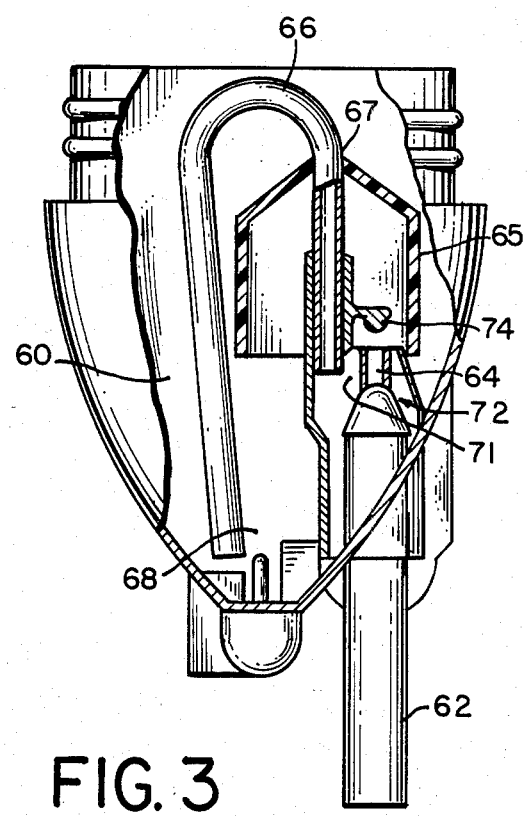
FIG. 2
FIG. 3

DISPOSABLE RADIOACTIVE AEROSOL INHALATION APPARATUS

This is a continuation of application Ser. No. 360,370, filed Apr. 30, 1982, abandoned.

BACKGROUND OF THE INVENTION

This invention relates to a radioactive aerosol inhalation apparatus which includes a disposable pulmonary inhalation device that is comprised of a means to generate properly sized radioactive particles for subsquent inhalation, and to a method which generates the particles and uses same. For various types of diagnostic testing and treating, it is necessary to have patients inhale radioactive materials in order, for example, to perform ventilation studies of the lung. In addition, it is well known that the hospital staff who handle radioactive materials need protection against the problems associated with ionizing radiation exposure and this apparatus provides for adequate shielding to meet this requirement. For flexibility, the apparatus is portable, the device is disposable, and the apparatus is inexpensive. The apparatus provides the capability to easily and safely add the radioactive solution to the nebulizer, for aerosolizing the radioactive solution to the proper particle size, and to collect the radioactive particles in a properly shielded filter.

This method of administering a radioactive aerosol is an improvement over existing modalities in that the radiation dose to the patient is less, the probability of radioactive contamination within the hospital room, as compared to other methods is diminished, and the flexibility to obtain images of various anatomical positions of the patient is increased.

Relevant prior art United States Letters Patents are:

| Number | Inventor(s) | Issue Date |
| --- | --- | --- |
| 3,762,409 | Lester | 10/02/72 |
| 3,881,463 | LeMon | 05/06/75 |
| 3,695,254 | Blum | 10/03/73 |
| 3,769,967 | Jones et al. | 11/06/73. |

SUMMARY OF THE INVENTION

The present invention relates to a new and improved aerosol inhalation method and apparatus that generates properly sized radioactive particles for performing ventilation studies of the lungs. A radioactive solution is added to a baffled nebulizer and the solution aerosolized using air or oxygen. The aerosolized radioactive particles are then breathed into the lung and data for assessing lung function may be recorded by means of a radiation particle counting device such as a scintillation camera and associated software. The radioactive aerosol is administered to the patient through a mouthpiece or face mask via a conduit of valved flexible tubing, the valving being in close proximity to the mouthpiece to minimize the volume of the passages from the valve head to the mouthpiece.

It is, therefore, a principal object of the present invention to provide an apparatus which includes a disposable radioactive aerosol inhalation device capable of allowing pulmonary ventilation tests that deliver proper-sized particles to lung areas, controlled delivery and recovery of radioactive aerosolized particles and shielding to minimize exposure of personnel to problems associated with ionizing radiation.

Another object of the invention is to provide an apparatus that incorporates a valve which is activated during the breathing cycle of the patient to assist in permitting the patient to inhale with the minimum of effort during the generation of radioactive aerosol from within the system.

Another object of the present invention is to provide a shielded portal to permit the safe and rapid addition of radioactive solution into the baffled nebulizer. The injection site is through a valve diaphragm that is positioned at an approximate 45 degree angle from the top of the baffled nebulizer.

A still further object of the invention is to provide an apparatus of the character described which will minimize the radiation exposure to the patient and technician administering the diagnostic test. Adequate shielding in the form of lead surrounds the baffled nebulizer and entrapping filter, reducing the problems associated with exposures to ionizing radiation.

Another object of the invention is to provide an appartus of the character described in which images or pictures from various anatomical positions can be taken further increasing the usefulness of this diagnostic method of evaluating diseases of the bronchus, the bronchioles, and the alveolar sites of the lung.

A further object of the invention is to provide an apparatus of the character described which will cause to reduce the radioactive contamination of the facilities, the equipment, and most importantly, the attending medical personnel.

An additional object of the invention is to provide a method of generating sized aerosolized radioactive particles and using same.

Other features and advantages of the invention will become more readily apparent from the following detailed description, when taken in conjunction with the accompanying drawings.

BRIEF DESCRIPTION OF THE DRAWINGS

FIG. 2 is a fragmentary perspective diagramatic view of a portion of the apparatus of FIG. 1 illustrating the angulated wye and valve through which radioactive solution is added to the baffled nebulizer.

FIG. 3 is a fragmentary perspective diagramatic view of a portion of the apparatus of FIG. 1 illustrating the modified nebulizer with its internal baffle.

DESCRIPTION OF THE PREFERRED EMBODIMENTS

Figure 1:
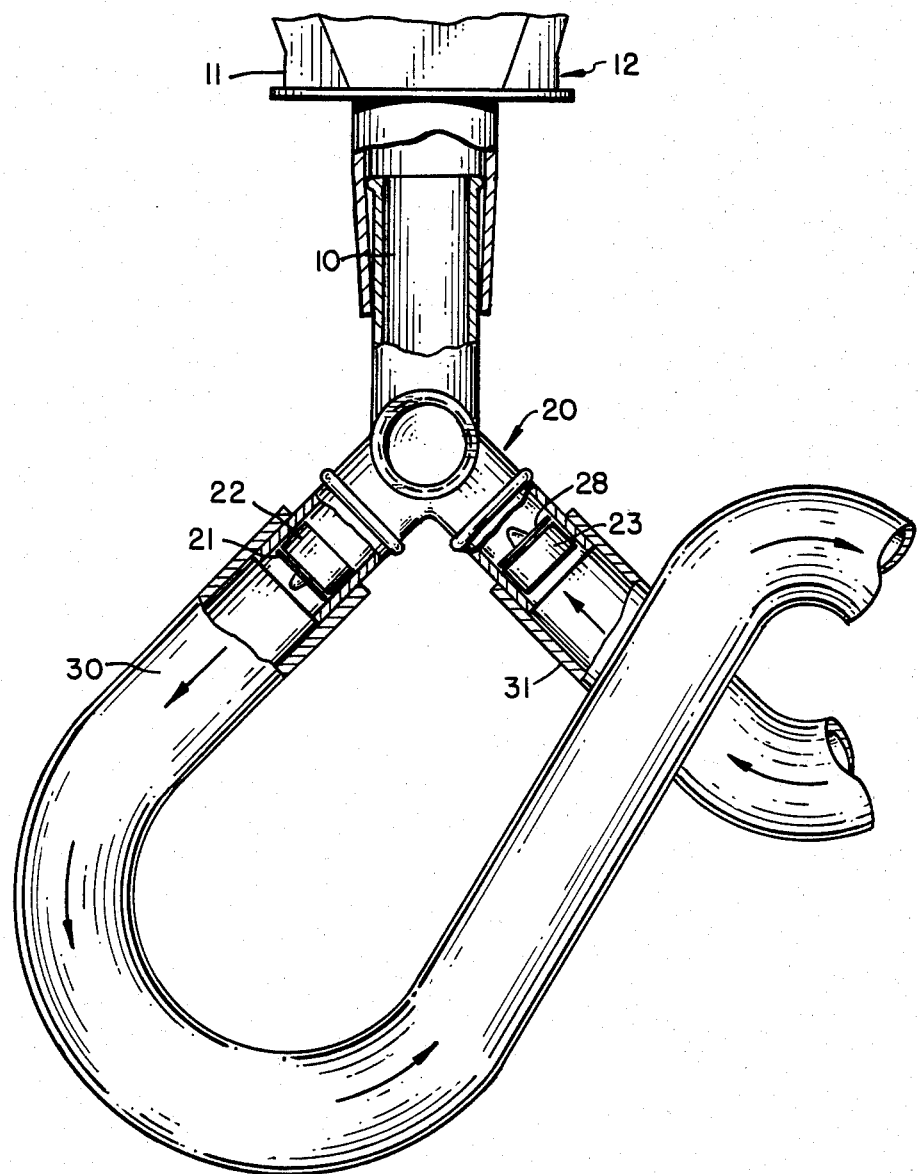
FIG. 1 is an elevational diagramatic perspective view of the aerosol inhalation apparatus constructed in accordance with the present invention.

Referring to FIG. 1, there is shown a disposable aerosol inhalation device for use in producing radioactive tagged particles in accordance with an embodiment of the invention. A patient (not shown) breathes through a mouthpiece 12 having flanges 11 to permit a tight fit in the mouth. The mouthpiece is attached to a tubular extension 10 of a wye 20 containing two one way valves, inlet valve 22 to the device and exit valve 23 from the device. The valves are positioned to effect the proper movement of radioactive particles through provided conduits 30, 31. As shown in FIG. 1, when the patient inhales, the diaphragm 28 of valve 23 opens and permits the radioactive particles to enter the mouthpiece and ultimately to deposit in the lungs. During inhalation, diaphragm 21 of valve 22 remains closed due to the pressure differential across valve 22. At exhalation, valve 23 closes and valve 22 opens to permit the exhalant to pass valve 22, travel through conduit 30, and into an entrapping filter 40 (FIG. 4).

Figure 4:
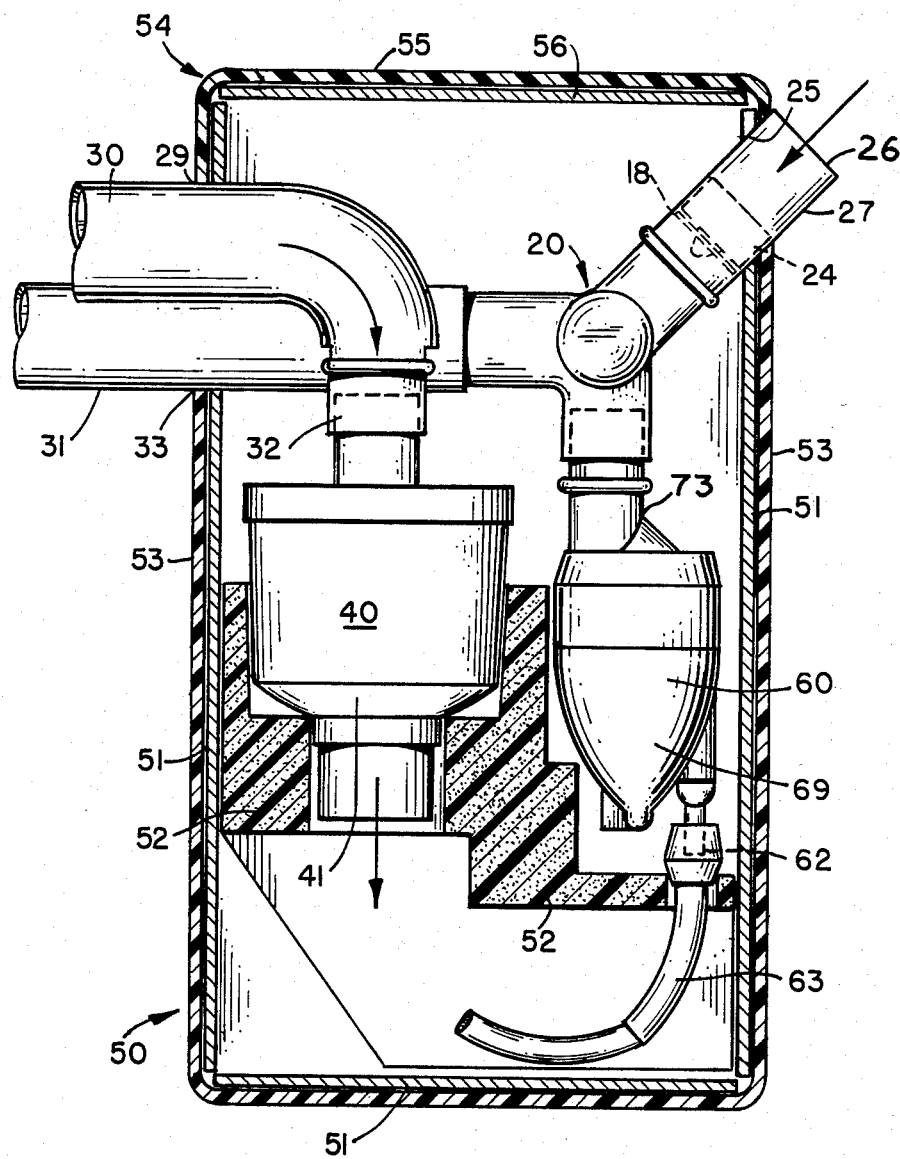
FIG. 4 is a fragmentary perspective diagramatic view of a portion of the apparatus of an apparatus which includes FIG. 1 illustrating the shielded container for the nebulizer and the entrapping filter.

FIG. 4 shows the operational technique as follows: The radiopharmaceutical liquid to be aerosolized is added to the system through the diaphragm 18 of valve 24 contained in wye leg 27. The wye leg 27 protrudes through shielded container 50 at portal 25, a downwardly extending slot being provided in the sidewall of the container 50 for this purpose. The entrance portal 26 to wye leg 27 is set at an angle to minimize direct radiation streaming from the solution of radioactive liquid contained in the baffled nebulizer 60 when the apparatus is in operation. The injected radioactive solution deposits in baffled nebulizer 60 at approximate level 69. Oxygen from a tank (not shown) is directed into the system at approximately 10 liters per minute via a flexible tube 63 which is connected to the bottom of nebulizer from the tank 62. The oxygen mixes with radioactive solution to form airborne particles. The airborne particles then traverse through conduit 31, through valve 23, and into a patient's lungs. The exhaled air, including aerosol passes through valve 22 to conduit 30 and into a filter 40, via tubular extension 32, and the aerosol becomes entrapped in the filter 40. The patient breathes the aerosolized radioactive particles until enough radiation from the patient's lungs is externally detected by sensing with radioactive detectors.

FIG. 2 illustrates entry port 26 of radioactive solution that enters the baffled nebulizer 60. The radioactive solution to be aerosolized is carried to entry port 26 in a shielded syringe to minimize radiation exposures to the administering technician and patient (both not shown). The entry port 26 and leg by 27, shown in FIG. 4 protrude from side 25 (FIG. 4) of the lead shielded container 50 at an approximate angle of forty-five degrees. The angulation of the entry port reduces the amount of radiation exposure to the administering technician due to streaming, once the radioactive solution has entered the nebulizer system. The solution enters the system through diaphragm 18 of valve 24. The needle of the syringe containing radioactive solution (not shown) pushes diaphragm 18 aside and while the orifice of the needle (not shown) protrudes past diaphragm 18, the radioactive solution is injected into the nebulizer system. Check valve 24 is approximately 22 millimeters in diameter. To ease patient's breathing, valve 24 also acts as an inlet valve in that each time the patient inhales, he receives a portion of air from the atmosphere. In addition, valve 24 acts as monitor to the patient's breathing function. The administering technician observes valve diaphragm movement 18 each time patient inhales to insure patient is breathing normally.

FIG. 3 illustrates nebulizer 60 fitted with an elongated conical baffle that permits proper sized radioactive particles to enter a patient's lungs. Oxygen enters nebulizer through stem 62. The oxygen gas passes through a nozzle assembly 72 extending into the container. The nozzle assembly 72 includes gas nozzle 64 and solution nozzle 71 with approximately perpendicular positioned orifices. Extending above the nozzle assembly is an elongated conical settling baffle 65 formed of plastic and having a volume of approximately three cubic centimeters. The settling baffle 65 reduces hyperdeposition of large particles typically greater than two microns from entering the patient's lungs. The aerosolized radioactive particles enter the baffle area at the diffuser orifice of the gas nozzle 64 and through sedimentation, impaction, and turbulence within the baffle 65, particles greater than two microns settle to the interior bottom portion 68 of the nebulizer 68, and particles typically less than two microns enter conduit (FIGS. 2, 4) above the nebulizer and are inhaled by the patient (not shown).

The top of the conical baffle has a symmetrical opening 67 of approximately three millimeters in diameter that permits entry of conduit tubing 66 that carries radioactive solution from the nebulizer reservoir to orifice 71. The radioactive solution exiting orifice 71 mixes with incoming oxygen and is aerosolized through orifice-diffuser arrangement which includes a diffuser 74. The particles are properly sized while engaging in turbulent action within the baffle 65.

FIG. 4 illustrates shielded container 50 which houses entrapping filter 40, baffled nebulizer 60 and supporting inserts 52. The container has an approximate volume of three liters and consists of outer plastic laminate 53, and lead shielding 51 comprising average thicknesses of two to four millimeters. The lead shielding is necessary to minimize radiation exposure to the administering technician and patient during the ventilation studies of the lung. Plastic or equivalent material insert 52 sets entrapping filter 40 in a fixed position using filter end portion 41 as a seat. Baffled nebulizer 60 is seated in similar fashion using reservoir end portions defined by level 69 and stem 62 thereof. Openings 32, 33 of approximately 25 millimeters in diameter are made through shielded container 50 to allow conduits 30, 31 and oxygen tube 63 to exit container. The additional opening 25 of approximately five millimeters is made through the container exposing entry port or injection site of the radioactive solution. The angle of opening 25, with respect to the horizontal in 90° and is made to minimize radiation streaming from shielded container 50. Cap 54 constructed of plastic laminate and lead of the previously described thickness together are of the plastic laminate 53 and lead shielding 51. The cap 54 is removable to permit easy access and exit of the disposable apparatus at commencement and termination of diagnostic procedures.

From the foregoing it will be seen that the pulmonary inhalation device of the present invention provides for a disposable device that generates properly sized radioactive particles having provisions for proper valving, proper shielding, and ease of operation. Further, the invention has been described with reference to particular embodiments, but it will be appreciated that variations within the spirit and scope of the invention will occur to those skilled in the art. For example, in FIG. 4, the oxygen tubing 63 could exit from another port in the shielding 50.

We claim:

1. An aerosol inhalation apparatus for supplying an aerosol mist containing radioactive tagged particles and air to a subject, comprising a reusable lead-shielded container having lid means, whereby the contents of the container are readily accessible, and a disposable radioactive aerosol inhalation device, the device including first and second conduit means in said said container and passing therethrough, mouthpiece means connected to the first and second conduit means externally of said container, valve means for controlling inhalation from said first conduit means and exhalation to said second conduit means, respectively, a nebulizer within said container and connected to said first conduit means, means positioned at least in part within the container and in fluid communication with said nebulizer for allowing introduction of radioactive solution from outside said container into said nebulizer, means associated with said nebulizer for generating an aerosolized mist carrying airborne radioactive tagged particles, means in fluid communication with a source of air and with said nebulizer for introducing a mixture of air and the mist into said first conduit means, and entrapping filter means in said container and connected to said second conduit means for removing the aerosol exhaled whereby the container may be reused and the device may be discarded after each use.

2. The aerosol inhalation apparatus according to claim 1, wherein said means carried by said container for allowing introduction of a radioactive solution into said nebulizer comprises a one way valve means in fluid communication with said nebulizer and with said first conduit means for permitting entry of atmospheric air into said nebulizer and into said first conduit means.

3. The aerosol inhalation apparatus according to claim 2, wherein said one way valve means includes an observable movable member to permit observation of inhalation frequency of a subject.

4. The aerosol inhalation apparatus according to claim 3, wherein said moveable member is a diaphragm of a one-way valve.

5. The aerosol inhalation apparatus according to claim 1, wherein said means for allowing introduction of a radioactive solution is an angulated valve part allowing a needle to extend into said container at an angle with respect to vertical to minimize exposure to radiation.

6. The aerosol inhalation apparatus according to claim 1, including a settling baffle in said nebulizer to generate properly sized aerosol particles of less than substantially two microns.

7. The aerosol inhalation apparatus according to claim 6, wherein said nebulizer includes a diffuser and gas orifice, said settling baffle being positioned above said diffuser and said gas orifice for permitting aerosol particles larger than substantially two microns to remain in said nebulizer.

8. An aerosol inhalation apparatus for supplying an aerosol mist containing radioactive charged particles and air to a subject, comprising a reusable generally cylindrical walled container having a closed bottom and an open top, lead shielding means within said wall and bottom of the container, the container having first, second and third openings formed therein, respectively, said openings being at the top portion of said container and being circumferentially spaced from each other, lead shielded lid means covering said container top portion, and a disposable pulmonary inhalation device including nebulizing means in said container, entrapping filter means within said container, means received in said first of said openings and including a conduit connected to said nebulizer means for introducing a radioactive liquid into said nebulizer means, means associated with said nebulizer means for generating an aerosolized mist having a plurality of radioactive tagged particles, inhalation conduit means received in said second of said openings and connected to a source of air and to said nebulizer means for receiving a mixture of air and the mist, and exhalation conduit means received in said third of said openings and connected to said filter means, whereby the container may be reused and the device may be discarded after each use.

* * * * *